United States Patent [19]
Mandai et al.

[11] Patent Number: 5,906,924
[45] Date of Patent: May 25, 1999

[54] PROCESS FOR PRODUCING TREHALOSE DERIVATIVES

[75] Inventors: Takahiko Mandai; Takashi Shibuya; Toshiyuki Sugimoto, all of Okayama, Japan

[73] Assignee: Kabushiki Kaisha Hayashibara Seibutsu Kaguku Kenkyujo, Okayama, Japan

[21] Appl. No.: 08/563,764

[22] Filed: Nov. 28, 1995

[30] Foreign Application Priority Data

Nov. 30, 1994 [JP] Japan ................................. 6-341189

[51] Int. Cl.$^6$ ............................. C12P 19/00; C12P 19/44; C07H 11/00; C07H 3/04
[52] U.S. Cl. ............................. 435/72; 435/74; 435/100; 435/200; 536/115; 536/118; 536/119; 536/120; 536/123.13
[58] Field of Search ...................... 536/119, 115, 536/118, 120, 123.13; 435/100, 72, 74, 200

[56] References Cited

U.S. PATENT DOCUMENTS

| | | | |
|---|---|---|---|
| 4,307,229 | 12/1981 | Liav et al. | 536/119 |
| 5,049,664 | 9/1991 | Yoshinaga et al. | 536/119 |
| 5,472,863 | 12/1995 | Maruta et al. | 435/200 |
| 5,538,883 | 7/1996 | Nishimoto et al. | 435/200 |

FOREIGN PATENT DOCUMENTS

| | | | |
|---|---|---|---|
| 0225774 | 11/1986 | European Pat. Off. | C07H 15/04 |
| 0 606 753 A2 | 12/1993 | European Pat. Off. | |
| 0636693 | 7/1994 | European Pat. Off. | C12N 9/90 |
| 0628630 | 12/1994 | European Pat. Off. | |
| 7-143876 | 6/1995 | Japan . | |

OTHER PUBLICATIONS

Lichtenthaler, Carohydrates inn Organic Raw Material, VCH Publishers, pp. 96–125, 1991.

Yoshimoto et al, Chemical and Biochemical Studies on Carbohydrate Esters, Chem. Pharm. Bull., vol. 30, No. 4, pp. 1169–1174, 1982.

Nishikawa et al, The Chemical Society of Japan, No. 10, pp. 1661–1666, 1982.

C.K. Lee, Developments in Carbohydrates–2, Applied Science, pp. 1–89, 1980.

Chemical and Pharmaceutical Bulletin, vol. 30, No. 4, Apr. 1982, Tokyo JP, pp. 1169–1174, XP000577043 K. Yoshimoto et al.: Chemical and biochemical studies on carbohydrate esters. XIII. Synthesis of 6–0–6,6'–Di–0–, and 4,6,4',6'–stearoyl–alpha, alpha–trehaloses.

Carbohydrate Research, vol. 137, 1985, Amsterdam NL, pp. 21–30, XP000577–41 G.A. Jeffrey & R. Nanni: "The crystal structure of anhydrous alpha, alpha–trehalose at −150A.".

Japan Society for Bioscienc, Biotechnology and Agrochemistry., vol. 59, No. 11, 1995, Tokyo, JP, pp. 2189–2190, XP000577071 T. Nishimoto et al.: "Existence of a novel enzyme converting maltose into trehalose.".

*Primary Examiner*—Francisco Prats
*Attorney, Agent, or Firm*—Browdy and Neimark

[57] ABSTRACT

High quality trehalose derivatives are readily prepared in a considerably high yield by reacting anhydrous trehalose with reactive reagents under anhydrous conditions. The trehalose derivatives can be used in a variety of fields in the production, the chemical synthesis, and the enzymatic synthesis of foods, cosmetics, pharmaceuticals, detergents and chemicals as surfactants, humectants, skin-beautifying agents, antitumor agents, and intermediates for chemical and enzymatic syntheses.

3 Claims, No Drawings

5,906,924

PROCESS FOR PRODUCING TREHALOSE DERIVATIVES

BACKGROUND OF THE INVENTION

1. Field of the Invention

The present invention relates to a novel preparation of trehalose derivatives, more particularly, to a preparation of trehalose derivatives including reacting anhydrous trehalose with a reactive agent under anhydrous conditions.

2. Description of the Prior Art

Recently, there has been interest in acid esters and alkyl ethers of trehalose such as fatty acid esters and sulfonic acid esters of trehalose. Nishikawa et al. reported in "*The Chemical Society of Japan*", No. 10, pp. 1,661–1,666 (1982) that trehalose esters of stearic acid, palmitic acid, and myristic acid strongly inhibited the growth of malignant tumors both in vivo and in vitro, and implied that these derivatives might be effective as antitumor agents. For example, Japanese Patent Laid-Open No. 290,808/92 discloses that trehalose sulfates satisfactorily retain the water valance of the skin and impart appropriate moisture to the skin. Therefore, these sulfates can be incorporated in some cosmetics as satisfactory humectants and skin-whitening agents. Trehalose ethers with alkyls of 8–25 carbon atoms are known as useful surfactants with a relatively high safety and activity.

As is disclosed by C. K. Lee in "*Developments in Food Carbohydrate-2*", pp. 1–89 (1980), published by Applied Science Publishers, and K. Yoshimoto in "*Chemical and Pharmaceutical Bulletin*", Vol. 30, No. 4, pp. 1,169–1,174 (1982), trehalose derivatives are generally prepared by reacting reactive reagents with crystalline trehalose hydrate under anhydrous conditions, and the quality and the yield of the final products especially depend on whether the moisture in the reaction systems can be eliminated to the highest possible degree. However, even when prepared in a solid form, crystalline trehalose hydrate generally contains about 10 w/w % moisture and only results in an unsatisfactory quality and poor yield when used intact. Therefore, crystalline trehalose hydrate is dried to an anhydrous state by using a desiccant such as diphosphorus pentaoxide, prior to use, but the removal of the water of crystallization is substantially difficult. Thus, satisfactorily high quality of trehalose derivatives could not be readily obtained in a considerably high yield and low cost.

SUMMARY OF THE INVENTION

In view of the foregoing, the object of the present invention is to provide a preparation of trehalose derivatives with a relatively high quality and in a considerably high yield and low cost.

The object of the present invention is attained by a preparation characterized in that it comprises a step of contacting anhydrous trehalose with a reactive agent under anhydrous conditions.

DETAILED DESCRIPTION OF THE INVENTION

The anhydrous trehalose used as a substrate in the present invention is substantially free from moisture. Therefore, trehalose derivatives with a relatively high quality can be readily obtained in a considerably high yield by using such anhydrous trehalose intact or after slight pre-drying.

Explaining now the present invention with reference to the following Experiments and Examples, the wording "trehalose derivatives" as referred to in the present specification includes those in general such as esters, ethers, halides, nitrogen-containing derivatives, and sulfur-containing derivatives of trehalose which are generally obtained by allowing reactive agents to react with anhydrous trehalose under anhydrous conditions. The wording "reactive agents" as referred to in the present specification means acids, salts, alcohols, ketones, halogens, amines, and reactive derivatives thereof which can form the present trehalose derivatives when reacted with anhydrous trehalose under anhydrous conditions. The present invention is applicable to chemical reaction systems in general where the moisture in the systems lowers the reactivity of reactive agents, causes unsatisfactory side reactions, inhibits the main reactions, and results in the deterioration of the quality and/or the reduction of the yield of the objective trehalose derivatives, as well as in the increment of their production cost.

The wording "anhydrous trehalose" as referred to in the present specification means anhydrous crystalline and anhydrous amorphous trehaloses which are substantially free from moisture, i.e. those which contain a moisture less than 3 w/w % when determined by the Karl Fischer's method. Such anhydrous trehalose can be also used in the present invention, and anhydrous crystalline trehalose is particularly useful because it generally contains a relatively high trehalose content and is obtainable in a relatively low cost. Depending on the reaction types and the uses of trehalose derivatives, the higher the trehalose content in anhydrous trehalose the more satisfactory for the present invention: Generally, anhydrous trehalose with a trehalose content of 70 w/w % or higher, preferably, 80 w/w % or higher, on a dry solid basis (d.s.b.) can be satisfactorily used.

Among anhydrous trehalose, anhydrous amorphous trehalose can be obtained by dissolving trehalose in a small amount of water, and lyophilizing the aqueous solution, or by drying it with spray drying, etc, at a temperature exceeding the melting point of anhydrous crystalline trehalose, usually, at a temperature over 100° C. For example, Japanese Patent Laid-Open No. 170,221/94 discloses a preparation of anhydrous crystalline trehalose which comprises concentrating a saccharide composition containing at least 60 w/w % trehalose, d.s.b., to give a moisture content less than 10 w/w %, preferably, into a syrupy product with a moisture content of higher than 2.0 w/w % but less than 9.5 w/w %, adding to the syrupy product 0.01–20 w/w %, d.s.b., of anhydrous crystalline trehalose as a seed crystal, keeping the contents at a temperature of 40–140° C. to crystallize trehalose, and collecting the formed anhydrous crystalline trehalose from the resultant massecuite, or drying the massecuite into a solid product. Generally, the anhydrous trehalose thus obtained does not substantially contain moisture, i.e. it only contains a moisture less than 3 w/w %.

The source and the origin of trehalose used as a material for anhydrous trehalose usable in the present invention are not specifically restricted. Any trehalose, including those obtained from cells of yeasts, those obtained by allowing complex enzyme systems comprising maltose- and trehalose-phosphorylases to act on maltose, those obtained by allowing maltose/trehalose converting enzymes to act on maltose to directly convert it into trehalose, and those obtained by enzymatically saccharifying partial starch hydrolysates can be used. With a view point of producing satisfactorily-high quality trehalose derivatives in a relatively low cost, material trehaloses obtained by the aforesaid third and fourth methods are satisfactorily used.

To produce trehalose from starch, non-reducing saccharide-forming enzymes, as disclosed in Japanese Patent Application Nos. 349,216/93, 90,705/94, 166,011/94 and 190,183/94, are allowed to act on reducing partial starch hydrolysates, which contain maltooligosaccharides with a glucose polymerization degree of at least 3 such as maltotriose, maltotetraose, maltopentaose and maltohexaose obtained by gelatinizing and liquefying starch with acids and/or α-amylase, to convert the maltooligosaccharides into non-reducing saccharides having a trehalose structure as an end unit. The non-reducing saccharides are subjected to the action of trehalose-releasing enzymes as disclosed in Japanese Patent Application Nos. 59,834/94, 79,291/94, 166, 126/94 and 190,180/94 to release trehalose from the saccharides. In this case, these different types of non-reducing saccharide-forming enzymes and trehalose-releasing enzymes can be used simultaneously or sequentially, and the combination use of these two different types of enzymes and debranching enzymes such as isoamylase and pullulanase can increase the trehalose content in the reaction mixtures. To directly convert maltose into trehalose, maltose/trehalose converting enzymes as disclosed, for example, in Japanese Patent Application Nos. 144,092/94, 156,399/94, 187,901/94 and 260,984/94, are allowed to act on maltose or saccharide compositions containing maltose. These specifications disclose processes for producing trehalose using maltose/trehalose converting enzymes, and any one of which can be used to produce the anhydrous trehalose used in the present invention. When a more highly purified trehalose is needed, the reaction mixtures obtained by those methods can be subjected to column chromatography using strong-acid cation exchangers in fixed-bed, moving-bed, or pseudo moving-bed methods to collect trehalose-rich fractions. The compositions and the fractions thus obtained contain at least 70 w/w % trehalose, d.s.b., and can be suitably used as a material for anhydrous trehalose.

Conventional methods can be used to react reactive agents with anhydrous trehalose under anhydrous conditions. For example, methods as disclosed by C. K. Lee in "*Developments in Food Carbohydrate*", pp. 1–89 (1980), published by Applied Science Publishers, and by K. Yoshimoto et al. in "*Chemical and Pharmaceutical Bulletin*", Vol. 30, No. 4, pp. 1,169–1,174 (1982), as well as those disclosed in "*Carbohydrates as Organic Raw Materials*" (1991), published by VCH Publishers, New, York, USA, can be used in the present invention, and appropriately chosen to meet to the objective trehalose derivatives.

Explaining now briefly the representative methods for producing trehalose derivatives, carbonic acid esters of trehalose such as trehalose acetate and trehalose benzoate can be obtained by reacting anhydrous trehalose with the corresponding acid anhydrides or acid halides in alkaline organic solvents such as pyridine. To produce trehalose sulfate, anhydrous trehalose is allowed to react with complexes of sulfur trioxide and dimethyl sulfoxide or pyridine in a stream of inert- or rare-gases. Fatty acid esters of trehalose, prepared by reacting trehalose with fatty acids such as lauric acid, myristic acid, palmitic acid, stearic acid, oleic acid, linoleic acid, and linolenic acid, can be obtained by the condensation reaction of anhydrous trehalose and these fatty acids in the presence of alkaline catalysts or by reacting anhydrous trehalose with its corresponding fatty acid halides. Ethers of trehalose can be obtained by reacting anhydrous trehalose with excessive amounts of its corresponding alcohols in the presence of acid catalysts or by reacting anhydrous trehalose with its corresponding alkyl halides in the presence of alkaline catalysts.

Depending on their use, the trehalose derivatives thus obtained are usually used intact after removing the remaining reactive agents and/or solvents by filtration, extraction, separation, separatory sedimentation, dialysis and distillation. If high-purity trehalose derivatives are needed, the intact or the partially purified trehalose derivatives can be treated with conventional methods used in this field such as thin layer chromatography, column chromatography, ion-exchange column chromatography, gas chromatography, distillation, and crystallization which are used to purify saccharides and saccharide derivatives. Two or more of these purification methods are used in combination to meet to final products. As is well known, trehalose has 8 reactive functional groups which participate in the normal substitution reaction where non-anomeric hydroxyl groups mainly act. This means that reaction products may contain a variety of trehalose derivatives with different degrees of substitution depending on the reaction types and conditions. Usually, these products can be used intact and, if necessary, may be treated with one or more of the aforesaid purification methods to isolate the desired component(s).

The trehalose derivatives obtained by the present process can be widely used in the fields of food-, cosmetic- and pharmaceutical-industries. The fatty acid esters and alkyl ethers of trehalose are relatively high in activity, and are useful as a surfactant for foods, cosmetics and pharmaceuticals. Depending on the types of fatty acids, the corresponding trehalose derivatives are expected to be used as antioncotic agents. Trehalose sulfates can be incorporated into cosmetics as humectants or skin-whitening agents, while trehalose halides are useful as intermediates for synthesizing a variety of derivatives.

The following experiments explain the effect and function of the present invention:

EXPERIMENT 1
Preparation of enzyme

EXPERIMENT 1—1
Preparation of non-reducing saccharide-forming enzyme

One hundred ml aliquots of a liquid nutrient culture medium (pH 7.0) containing 2.0 w/v % maltose, 0.5 w/v % peptone, 0.1 w/v % yeast extract, 0.1 w/v % disodium hydrogen phosphate, and 0.1 w/v % sodium dihydrogen phosphate were placed in 500-ml Erlenmeyer flasks, and sterilized by autoclaving at 120° C. for 20 min. After cooling the flasks, a seed of Rhizobium sp. M-11 (FERM BP-4130) was inoculated into each medium and incubated at 27° C. for 24 hours under rotatory shaking conditions to obtain a seed culture. Thereafter, 20 L aliquots of a fresh preparation of the same nutrient culture medium were placed in 30-L jar fermenters, sterilized, and inoculated with one v/v of the seed culture, followed by the incubation at a pH of 6–8 and at 30° C. for 24 hours under aeration-agitation conditions.

About 18 L of the resultant culture was placed in a super high-pressure cell disrupting the apparatus to disrupt cells, and the suspension was centrifuged to obtain a supernatant. To about 16 L of the supernatant was added ammonium sulfate to give a saturation degree of 20 w/v %, and the solution was allowed to stand at 4° C. for an hour and centrifuged to remove sediment. The supernatant thus obtained was mixed with ammonium sulfate to give a degree of saturation 60 w/v %, allowed to stand at 4° C. for 24 hours, centrifuged to collect sediment which was then dissolved in a minimum amount of 10 mM phosphate buffer (pH 7.0), dialyzed against 10 mM phosphate buffer (pH 7.0) for 24 hours, and centrifuged to remove insoluble substances. The resultant supernatant was fed to a column packed with "DEAE-TOYOPEARL®", an ion exchanger commercialized by Tosoh Corporation, Tokyo, Japan, which had been previously equilibrated with 10 mM phosphate buffer (pH 7.0), and eluted from the column with a linear gradient of sodium chloride increasing from 0M to 0.5M in 10 mM phosphate buffer (pH 7.0). Fractions with an enzymatic activity were collected from the eluate, pooled, dialyzed against 50 mM phosphate buffer (pH 7.0) containing 2M ammonium sulfate for 10 hours, and centrifuged to remove insoluble substances. The resultant supernatant was fed to a column packed with "BUTYL-TOYOPEARL®", a gel for hydrophobic column chromatography commercialized by Tosoh Corporation, Tokyo, Japan, which had been previously equilibrated with 50 mM phosphate buffer (pH 7.0) containing 2M ammonium sulfate, and eluted from the column with a linear gradient of sodium chloride decreasing from 2M to 0M in 50 mM phosphate buffer (pH 7.0). Fractions with an enzymatic activity were collected from the eluate, pooled, fed to a column packed with "TOYOPEARL® HW-55", a gel for gel filtration column chromatography commercialized by Tosoh Corporation, Tokyo, Japan, which had been previously equilibrated with 50 mM phosphate buffer (pH 7.0), and eluted from the column with 50 mM phosphate buffer (pH 7.0) to collect fractions with an enzymatic activity. The resultant purified non-reducing saccharide-forming enzyme was a protein with a specific activity of about 195 units/mg protein, and the yield was about 220 units per one L of the culture.

Throughout the present specification, the non-reducing saccharide-forming enzyme activity is assayed by the following method and expressed by the value of units: Place in a test tube 4 ml of 50 mM phosphate buffer (pH 7.0) containing 1.25 w/v % maltopentaose, add one ml of an enzyme solution to the tube, incubate the mixture at 40° C. for 60 min to effect enzymatic reaction, and heat the resultant mixture at 100° C. for 10 min to suspend the reaction. Dilute the reaction mixture with distilled water by 10 fold, and assay the reducing power by the Somogyi-Nelson's method. As a control, an enzyme solution, preheated at 100° C. for 10 min to inactivate the enzyme, was treated similarly as above. One unit activity of the non-reducing saccharide-forming enzyme is defined as the amount of enzyme which reduces the reducing power corresponding to one $\mu$mol of maltopentaose per min.

EXPERIMENT 1-2
Preparation of trehalose-releasing enzyme

One hundred ml aliquots of a liquid nutrient culture medium (pH 7.0) containing 2.0 w/v % "PINE-DEX #4", a partial starch hydrolysate commercialized by Matsutani Chemical Ind., Co., Ltd., Hyogo, Japan, 0.5 w/v % peptone, 0.1 w/v % yeast extract, 0.1 w/v % disodium hydrogen phosphate, and 0.1 w/v % sodium dihydrogen phosphate were placed in 500-ml Erlenmeyer flasks, and sterilized by autoclaving at 120° C. for 20 min. After cooling the flasks, a seed of Rhizobium sp. M-11 (FERM BP-4130) was inoculated into each medium and incubated at 27° C. for 24 hours under rotatory shaking conditions to obtain a seed culture. Thereafter, 20 L aliquots of a fresh preparation of the same medium were placed in 30-L jar fermenters, sterilized, and inoculated with one v/v of the seed culture, followed by the incubation at a pH of 6–8 and at 30° C. for 24 hours under aeration-agitation conditions.

An about 18 L of the resultant culture was treated similarly as in Experiment 1-1 to disrupt cells, and the suspension was purified to obtain a trehalose-releasing enzyme with a specific activity of about 240 units/mg protein. The yield was about 650 units per one L of the culture.

Throughout the present specification, the trehalose-releasing enzyme activity is assayed by the following method and expressed by the value of units: Place in a test tube 4 ml of 50 mM phosphate buffer (pH 7.0) containing 1.25 w/v % $\alpha$-maltotriosyltrehalose, add one ml of an enzyme solution to the tube, and incubate the mixture at 40° C. for 30 min to effect enzymatic reaction. One ml of the reaction mixture was placed in a test tube, add 2 ml of Somogyi copper solution to the mixture to suspend the reaction, and assay the reducing power by the Somogyi-Nelson's method. As a control, an enzyme solution, preheated at 100° C. for 10 min to inactivate the enzyme, was treated similarly as above. One unit activity of the trehalose-releasing enzyme is defined as the amount of enzyme which increases the reducing power corresponding to one $\mu$mol of glucose per min.

EXPERIMENT 2
Preparation of trehalose

EXPERIMENT 2-1
Preparation of anhydrous crystalline trehalose

One part by weight of potato starch was suspended in 10 parts by weight of water and mixed with a bacterial liquefying $\alpha$-amylase in usual manner, followed by heating the mixture to 90° C. to gelatinize and liquefy the contents up to give a DE (dextrose equivalent) 0.5, then immediately heating the resultant to 130° C. to suspend the enzymatic reaction. The liquefied starch was promptly cooled to 45° C., then mixed with one unit/g starch, d.s.b., of the non-reducing saccharide-forming enzyme obtained in Experiment 1-1, one unit/g starch, d.s.b., of the trehalose releasing enzyme obtained in Experiment 1-2, and 200 units/g starch, d.s.b., of an isoamylase specimen commercialized by Hayashibara Biochemical Laboratories, Inc., Okayama, Japan, followed by saccharifying the contents for 48 hours while keeping the pH at about 6.0 to obtain a reaction mixture containing 80.5 w/w % trehalose, d.s.b. The reaction mixture was in usual manner decolored with an activated charcoal, desalted and purified with an ion exchanger, concentrated up to 75 w/w %, transferred to a crystallizer, heated to 50° C., mixed with one w/w %, d.s.b., of crystalline trehalose hydrate, and cooled to 30° C. during 24 hours under gently stirring conditions. The resultant massecuite containing the crystalline trehalose hydrate was separated with a basket-type centrifuge, and the collected crystal was sprayed with a small amount of water to obtain crystalline trehalose hydrate containing 99.0 w/w % trehalose in a yield of 47% to the material starch, d.s.b.

EXPERIMENT 2-2
Preparation of anhydrous crystalline trehalose

A portion of the crystalline trehalose hydrate obtained by the method in Experiment 2-1 was provided, dissolved in a small amount of water by heating, transferred to a vessel, and concentrated into a syrup with a moisture content of 9.5 w/w % under a reduced pressure. The syrup was placed in a crystallizer, mixed with as a seed crystal one w/w % of anhydrous crystalline trehalose, d.s.b., and crystallized at 100° C. for 5 min under stirring conditions. The resultant massecuite was distributed into plastic plain vessels and aged by standing at 70° C. for 3 hours. Thereafter, the solidified massecuites in a block form were removed from the vessels and pulverized in usual manner to obtain a powdery anhydrous crystalline trehalose with a moisture content of about one w/w % in a yield of about 90% to the material, d.s.b.

EXPERIMENT 2-3

Preparation of anhydrous amorphous trehalose

A portion of the crystalline trehalose hydrate obtained by the method in Experiment 2-1 was dissolved in water to give a concentration of about 40 w/w %, lyophilized, pulverized to obtain an anhydrous amorphous trehalose powder with a moisture content of about 2 w/w % in a yield of about 100% to the material, d.s.b.

EXPERIMENT 3

Preparation of octaacetyltrehalose

Sixty-five g dry pyridine containing 50 g acetic anhydride was placed in a reaction container, cooled to 0° C., and mixed with 3 g either of the crystalline trehalose hydrate, anhydrous crystalline trehalose, and anhydrous amorphous trehalose obtained in Experiment 2-1 to 2-3, respectively, followed by completely dissolving the saccharide in the solvent under gentle stirring conditions. The solution was allowed to stand at ambient temperature for 18 hours to react the contents, and the reaction mixture was poured into iced water, allowed to stand for a while, and separated by decantation to collect a layer of the organic solvent, followed by concentrating the layer. The concentrate was analyzed by conventional method using gas chromatography to quantify the formed octaacetyltrehalose, followed by macroscopically observing the color of the octaacetyltrehalose. The results are shown in the Table.

TABLE

| Substrate | Yield of octaacetyltrehalose (%) | Degree of color | Judgement |
| --- | --- | --- | --- |
| Crystalline trehalose hydrate | 60 | ++ | Control |
| Anhydrous crystalline trehalose | 98 | ± | Present invention |
| Anhydrous amorphous trehalose | 97 | ± | Present invention |

Note: In Table, the symbol "±" means that a product slightly colored, and the symbol "++" means that a product strongly colored when observed macroscopically.

The results in the Table show that a strongly colored octaacetyltrehalose is obtained with a theoretical yield of 60% when crystalline trehalose hydrate was used as a substrate, while a high quality octaacetyltrehalose is obtained with almost a theoretical yield when anhydrous crystalline trehalose and anhydrous amorphous trehalose were used as substrates. The data show that the present invention using anhydrous trehalose as a substrate significantly improves the yield and quality of trehalose derivatives as compared with those obtained by the methods using crystalline trehalose hydrate.

The following examples explain the present invention:

EXAMPLE 1

Trehalose linoleate

Two hundred ml of anhydrous pyridine and the anhydrous amorphous crystalline trehalose, obtained by the method in Experiment 2-3, were placed in a reaction container, and mixed with 4 g of thiazolithione-linoleic acid amide dissolved in 5 ml anhydrous pyridine. To the reaction mixture was added 85 mg of 60 w/w % oily sodium hydride, and the resultant was reacted at ambient temperature for 2 hours. The reaction mixture was admixed with 1.5 ml of saturated aqueous ammonium chloride solution, followed by removing pyridine in vacuo to obtain 8.5 g residue. The purification of the residue using silica gel chromatography resulted in 5.3 g trehalose linoleate with an average substitution degree of 1.4.

The tasteless and odorless product with a considerably high activity can be arbitrarily used in foods, cosmetics and pharmaceuticals as a safety non-ionic surfactant. As a control, the crystalline trehalose hydrate obtained by the method in Experiment 2-1 was reacted similarly as above, resulting in only 2.3 g strongly-colored trehalose linoleate.

EXAMPLE 2

Trehalose myristate

Two hundred and twenty g of anhydrous crystalline trehalose, obtained by the method in Experiment 2-2, was dissolved in 800 ml of N,N'-dimethylformamide, admixed with 60 g of myristic acid methylester and 4 g of calcium carbonate, and subjected to an enzymatic reaction at a temperature of 85–95° C. for 24 hours under a reduced pressure of 100–200 mmHg. Thereafter, the organic solvent was removed from the reaction mixture in vacuo, and the residue was soaked twice in 300 ml acetone. The extracts were pooled and washed with benzene and oil ether to obtain a viscous oily product which was then soaked again in 300 ml acetone. The extract thus obtained was cooled, and the formed sediment was collected and dried into 310 g trehalose myristate with an average degree of substitution of 1.7.

The tasteless and odorless product with a considerably high activity can be arbitrarily used in foods, cosmetics and pharmaceuticals as a safe non-ionic surfactant. Because the product has an activity of inhibiting the growth of malignant tumors, it can be also used as an effective ingredient for pharmaceuticals. As a control, the crystalline trehalose hydrate, obtained by the method in Experiment 2-1, was reacted similarly as above to obtain only 90 g strongly-colored trehalose myristate.

EXAMPLE 3

Trehalose dodecyl ether

Three hundred and ninety g of n-dodecanol was placed in a reaction container, heated to 125° C., and admixed with one g of p-toluene sulfonate as a catalyst, followed by reducing the inner pressure of the container to 5–10 mmHg. One hundred g of anhydrous amorphous trehalose, obtained by the method in Experiment 2-3, was suspended in 130 g n-dodecanol, and the suspension was added to the container drop by drop at a rate of 2.3 g/min during 100 min. The resultant reaction mixture was neutralized with saturated sodium carbonate, followed by removing intact n-dodecanol to obtain about 140 g of a composition containing 79.9 w/w % trehalose dodecyl ether, d.s.b.

The product with a relatively high activity can be arbitrarily used as a safe surfactant in detergents for laundry and kitchen, and those in general including shampoos. As a control, crystalline trehalose hydrate, obtained by the method in Experiment 2-1, was reacted similarly as above, resulting in an about 80 g composition containing 27.5 w/w % strongly-colored trehalose dodecyl ether, d.s.b.

EXAMPLE 4

Trehalose sulfate

One part by weight of anhydrous amorphous trehalose, obtained by the method in Experiment 2-3, was placed in a reaction container, and mixed drop by drop with 5 parts by weight of sulfur trioxide/dimethylformamide complex under a stream of nitrogen gas. The mixture was successively subjected to an enzymatic reaction at ambient temperature for 4 hours and at 70° C. for one hour. The reaction mixture was neutralized with an adequate amount of 5N sodium hydroxide, mixed with 5-fold volumes of methyl alcohol, and allowed to stand for a while, followed by collecting the formed sediment by filtration by means of suction to obtain trehalose sulfate with an average degree of substitution 7.7 in a yield of about 95 w/w %, d.s.b.

The product with a relatively-high quality can be used in cosmetics in general such as humectants and skin-beautifying agents. As a control, crystalline trehalose hydrate, obtained by the method in Experiment 2-1, was subjected to an enzymatic reaction similarly as above to obtain strongly-colored trehalose sulfate with an average substitution degree of 6.5 in a yield of about 63 w/w %, d.s.b.

EXAMPLE 5
Trehalose sulfate

EXAMPLE 5-1
Preparation of maltose/trehalose converting enzyme

To 500-ml flasks were added 100 ml aliquots of a liquid nutrient culture medium (pH 7.2) consisting of 2.0 w/v % glucose, 0.5 w/v % polypeptone, 0.1 w/v % yeast extract, 0.1 w/v % dipotassium hydrogen phosphate, 0.06 w/v % sodium dihydrogen phosphate, 0.05 w/v % magnesium sulfate heptahydrate, 0.5 w/v % calcium carbonate, and water, and the flasks were sterilized by heating at 115° C. for 30 min, cooled, inoculated with a seed of Pimerobacter sp. R48 (FERM BP-4315), followed by the cultivation at 27° C. for 24 hours under a stirring condition of 200 rpm to obtain a seed culture. Thereafter, 20-L aliquots of a fresh preparation of the same liquid nutrient culture medium were placed in 30-L jar fermenters, sterilized similarly as above, cooled to 27° C., inoculated with one v/v % of the seed culture, and cultured at a pH of 6.0–8.0 and at 27° C. for 40 hours under aeration-agitation conditions.

The resultant culture was centrifuged, and about 0.5 kg of the collected wet cells were suspended in 10 mM phosphate buffer (pH 7.0) and disrupted in the usual manner, followed by centrifuging the resultant suspension to obtain an about 4.5 L crude enzyme solution. Ammonium sulfate was added to the suspension to give a degree of saturation about 30 w/v %, salted out by standing at 4° C. for 4 hours, and centrifuged to obtain a supernatant. Ammonium sulfate was added to the supernatant to give a degree of saturation 80 w/v %, allowed to stand at 4° C. overnight, and centrifuged to collect sediment which was then dissolved in a small amount of 10 mM phosphate buffer (pH 7.0), and dialyzed against 10 mM phosphate buffer (pH 7.0) for 24 hours. The dialyzed inner solution was centrifuged, and the supernatant was fed to a column packed with DEAE TOYOPEARL®, a resin for ion-exchange column chromatography commercialized by Tosoh Corporation, Tokyo, Japan, and eluted with a linear gradient of sodium chloride increasing from 0M to 0.4M in 10 mM phosphate buffer (pH 7.0). From the eluate, fractions with the objective enzyme activity were collected, pooled, dialyzed against 10 mM phosphate buffer (pH 7.0) containing one M ammonium sulfate for 10 hours, and centrifuged to obtain a supernatant. The supernatant was fed to a column packed with "BUTYL TOYOPEARL®", a resin for hydrophobic column chromatography commercialized by Tosoh Corporation, Tokyo, Japan, which had been equilibrated with 10 mM phosphate buffer (pH 7.0) containing one M ammonium sulfate, and eluted with a linear gradient of ammonium sulfate decreasing from 1M to 0M in 10 mM phosphate buffer (pH 7.0). Fractions with an enzyme activity were collected from the eluate, pooled, fed to a column packed with "MONO Q HR5/5", an ion exchanger for ion exchange column chromatography commercialized by Pharmacia LKB Biotechnology AB Uppsala, Sweden, which had been equilibrated with 10 mM phosphate buffer (pH 7.0), and eluted from the column with a linear gradient of sodium chloride increasing from 0M to 0.5M in 10 mM phosphate buffer (pH 7.0), followed by collecting fractions with the objective enzyme activity. The resultant purified maltose/trehalose converting enzyme had a specific activity of about 17 units/mg protein in a yield of about 46 units per one L of the culture.

Throughout the present specification, the activity of the maltose/trehalose converting enzyme was assayed by the following method and expressed by the value of activity (unit): Place in a test tube one ml of 10 mM phosphate buffer (pH 7.0) containing 20 w/v % maltose, add one ml of an appropriately diluted enzyme solution to the tube, enzymatically react the contents by incubating at 25° C. for 60 min, heat the reaction mixture at 100° C. for 10 min to suspend the reaction. Dilute the reaction mixture with 50 mM phosphate buffer (pH 7.5) by 11-fold, place 0.4 ml of the diluted solution in a test tube, add 0.1 ml of a solution containing one unit/ml trehalase to the tube, incubate the tube at 45° C. for 120 min, and quantify the glucose content in the reaction mixture by the glucose oxidase method. In parallel, provide as a control a system using an enzyme solution preheated at 100° C. for 10 min to inactivate the enzyme, and treat the system similarly as above. Based on the quantified glucose content, estimate the formed trehalose content. One unit activity of the maltose/trehalose converting enzyme is defined as the amount that forms one μmol trehalose per min under the above conditions.

Example 5-2
Preparation of anhydrous crystalline trehalose

Corn starch was suspended in water to give a concentration of 15 w/w %, adjusted to pH 5.5, mixed with 2 units/g starch, d.s.b., of "SPITASE HS", a liquefying α-amylase commercialized by Nagase Biochemicals, Ltd., Kyoto, Japan, and heated at 90° C. under stirring conditions to gelatinize and liquefy the starch. The liquefied starch was autoclaved at 120° C. for 20 min to inactivate the enzyme, promptly cooled to 55° C., adjusted to pH 5.0, mixed with an isoamylase specimen commercialized by Hayashibara Biochemical Laboratories, Inc., Okayama, Japan, and a β-amylase specimen commercialized by Nagase Biochemicals, Ltd., Tokyo, Japan, in respective amounts of 300 units and 20 units per g starch, d.s.b., and allowed to react for 24 hours to obtain a reaction mixture containing 92 w/w % maltose, d.s.b. The reaction mixture was heated at 100° C. for 20 min to inactivate the remaining enzyme, heated to 20° C., adjusted to pH 7.0, mixed with 1.5 units/g starch, d.s.b., of the maltose/trehalose converting enzyme obtained in Example 5-1, and enzymatically reacted for 72 hours to obtain a reaction mixture containing 71 w/w % trehalose, d.s.b. The resultant reaction mixture was heated at 95° C. for 10 min to inactivate the remaining enzyme, cooled, purified similarly as in Experiment 2-1, and concentrated up to give a moisture content of 9.5 w/w %. The concentrate was placed in a crystallizer, admixed with one w/w %, d.s.b., of a powdery anhydrous crystalline trehalose as a seed, and crystallized at 110° C. for 10 min under stirring conditions. The resultant massecuite was distributed to plastic vessels and aged by standing at 70° C. for 3 hours. Thereafter, the solidified massecuite in a block form was removed from each vessel, pulverized in usual manner, and subjected to fluidized-bed drying to obtain a powdery anhydrous crystalline trehalose with a moisture content of about 2 w/w % in a yield of about 95% to the material starch, d.s.b.

EXAMPLE 5-3
Preparation of trehalose sulfate

One hundred g of anhydrous crystalline trehalose, obtained by the method in Example 5-2, was placed in a container, and sulfated by the method in Example 4 to obtain about 240 g of a composition containing trehalose sulfate with an average degree of substitution about 8.

The product with a relatively high quality can be arbitrarily used as a humectant or a skin-beautifying agent in cosmetics in general.

As is described above, the present invention enables production of relatively high quality trehalose derivatives, which could not have been readily obtained by conventional methods, by reacting anhydrous trehalose with reactive reagents under anhydrous conditions. Unlike crystalline trehalose hydrate, anhydrous trehalose has no water of crystallization, so that it greatly reduces or even omits the drying step required for pre-reaction and leads to a considerably high reduction of the production cost of trehalose derivatives. The trehalose derivatives, obtained by the present invention, can be used in a variety of fields in the production, the chemical synthesis, and the enzymatic synthesis of foods, cosmetics, pharmaceuticals, detergents and chemicals as surfactants, humectants, skin-beautifying agents, antitumor agents, and intermediates for chemical and enzymatic syntheses.

While there has been described what is at present considered to be the preferred embodiments of the invention, it will be understood the various modifications may be made therein, and it is intended to cover in the appended claims all such modifications as fall within the true spirit and scope of the invention.

We claim:

1. In a process for producing a trehalose derivative selected from the group consisting of carbonic acid esters, sulfates, fatty acid esters, and ethers of trehalose, wherein trehalose is reacted with a reactive agent selected from the group consisting of acids, salts, alcohols, ketones, halogens, amines, and derivatives thereof under anhydrous conditions to substitute at least one element or radical of trehalose;

the improvement comprising using as the starting trehalose an anhydrous trehalose with a moisture content of not more than about 2% as determined by the Karl Fischer's method and having a purity of at least 99.0 w/w % on a dry solid basis.

2. The process of claim 1, wherein said anhydrous trehalose is anhydrous crystalline- or anhydrous amorphous-trehalouse.

3. In a process for producing a trehalose derivative selected from the group consisting of carbonic acid esters, sulfates, fatty acid esters, and ethers of trehalose, the improvement in said process consisting essentially of:

(a) contacting a partial starch hydrolysate with a non-reducing saccharide-forming enzyme to form a non-reducing saccharide having a trehalose structure as an end unit;

(b) contacting said non-reducing saccharide with a trehalose-releasing enzyme to release trehalose;

(c) drying or crystallizing the formed trehalose into an anhydrous crystalline trehalose with a moisture content of not more than about 2% as determined by the Karl Fischer's method and having a purity of at least 99.0 w/w %, on a dry solid basis;

(d) reacting a reactive agent, selected from the group consisting of acids, salts, alcohols, ketones, halogens, amines, and derivatives thereof, with the anhydrous trehalose obtained in step (c) under anhydrous conditions to substitute one or more elements or radicals of trehalose; and (e) collecting the trehalose derivative so produced.

* * * * *